United States Patent [19]
Lang et al.

[11] 4,129,656
[45] Dec. 12, 1978

[54] THIAZOLIDINE DERIVATIVES, SALIDIURETIC COMPOSITIONS AND METHODS OF EFFECTING SALIDIURESIS EMPLOYING THEM

[75] Inventors: Hans-Jochen Lang, Altenhain; Roman Muschaweck, Frankfort am Main, both of Fed. Rep. of Germany

[73] Assignee: Hoechst Aktiengesellschaft, Frankfurt am Main, Fed. Rep. of Germany

[21] Appl. No.: 760,411

[22] Filed: Jan. 18, 1977

[30] Foreign Application Priority Data

Jan. 20, 1976 [DE] Fed. Rep. of Germany ....... 2601791

[51] Int. Cl.² ................. C07D 277/04; C07D 277/60; A61K 31/425; A61K 31/435

[52] U.S. Cl. .................... 424/263; 424/270; 260/306.7 R; 260/501.1; 260/501.19; 546/280; 546/270; 546/331

[58] Field of Search .................... 260/306.7 R, 455 A, 260/294.8 D, 294.8 B; 424/270, 263

[56] References Cited

U.S. PATENT DOCUMENTS

| 3,671,534 | 6/1972 | Houlihan et al. | 424/270 |
| 4,083,979 | 4/1978 | Lang et al. | 424/251 |

Primary Examiner—Nicholas S. Rizzo
Assistant Examiner—Diana G. Rivers
Attorney, Agent, or Firm—Curtis, Morris & Safford

[57] ABSTRACT 4-(Sulfamoyl-phenyl)-4-hydroxy-thiazolidine-derivatives having salidiuretic activity and a process for their manufacture.

14 Claims, No Drawings

THIAZOLIDINE DERIVATIVES, SALIDIURETIC COMPOSITIONS AND METHODS OF EFFECTING SALIDIURESIS EMPLOYING THEM

The present invention relates to thiazolidine derivatives and to a process for preparing them.

The subject-matter of the present invention are thiazolidine derivatives of the general formula I

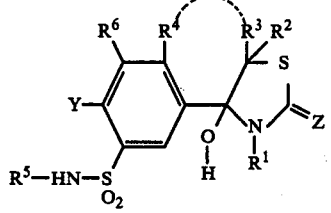

in which $R^1$ represents alkyl or alkenyl having 1 to 4 carbon atoms, a pyridylmethyl radical, $R^2$ and $R^3$ are hydrogen or alkyl having 1 to 3 carbon atoms, $R^4$ and $R^6$ are hydrogen or halogen, however, one of the radicals $R^4$ or $R^6$ standing for hydrogen, $R^3$ and $R^4$ may be linked with each other cyclically via a straight or branched methylene chain having 1 to 5 carbon atoms, $R^5$ is hydrogen, lower alkyl having 1 to 4 carbon atoms or benzyl, the aromatic nucleus of the said benzyl radical optionally being by chlorine or methyl, Y is halogen and Z is oxygen or sulfur.

The invention furthermore provides a process for the preparation of the compounds of the general formula I, which comprises reacting (a) compounds of the general formula II

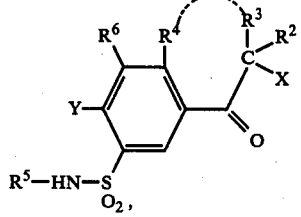

in which $R^2$ to $R^6$ and Y are defined as above and X stands for the radical of an activated ester of an inorganic or organic acid, with thiocarbamic acid derivatives III

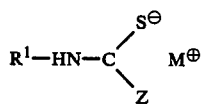

and/or the salts thereof, in whih $R^1$ and Z are defined as above and M stands for hydrogen or an organic or inorganic cation, (b) reacting compounds of the general structure IV

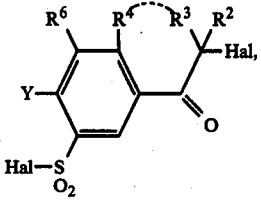

in which $R^2$ to $R^4$, $R^6$ and Y are defined as above and Hal stands for halogen, with the compounds of the general formula III to give thiazolidine-sulfochlorides of the general formula V

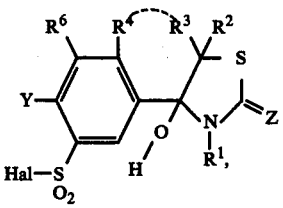

ps in which $R^1$ to $R^4$, $R^6$, Y, Z and Hal are defined as above, and reacting the compounds V, optionally without their isolation, with ammonia or a primary amine of the formula VI

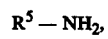

in which $R^5$ is defined as above, (c) reacting compounds of the general formula VII

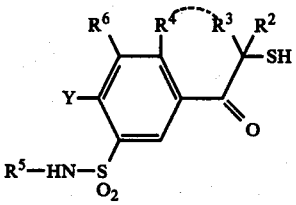

with compounds of the formula VIII

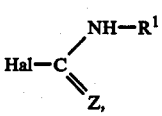

in which $R^1$ to $R^6$, Y and Z are defined as above and Hal stands for chlorine and bromine, (d) reacting compounds of the general formula VII with alkylisocyanates or alkyl-isothiocyanates of the formula IX

in which $R^1$ and Z are defined as above, and (e) treating compounds of the general formula X

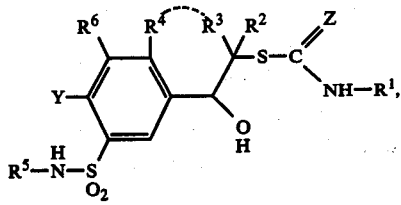

in which $R^1$ to $R^6$ are defined as above, with an oxidizing agent.

Compounds I and V may also be present in their tautomeric forms Ia and Va:

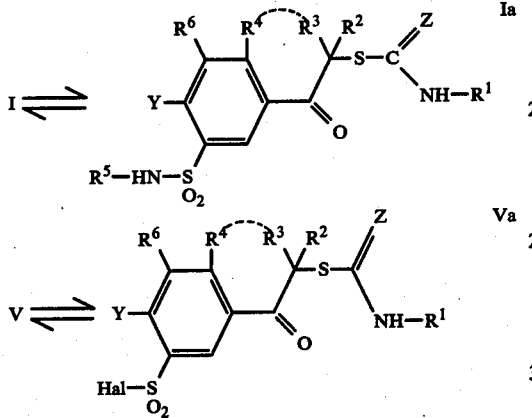

The compounds of the invention may, in addition, be present in their possible geometrical isomeric structures.

For the sake of simplicity, in the following only one of the possible isomeric or tautomeric forms is indicated for the compounds of the invention.

The alkyl or alkenyl radicals in the substituents $R^1$ to $R^5$ may be straight-chained as well as branched.

The method described under (a) above is advantageously carried out by reacting the ketones II with compounds III in a molar ratio of 1:1 to 1:1.5. Higher molar excess amounts of thiocarbamic acid derivative III generally do not give significant advantages. The reaction is advantageously carried out in an inert solvent, such as a polar organic solvent, for example, dimethyl formamide, dimethyl acetamide, dioxan, tetrahydrofuran, acetonitrile, nitromethane, diethyleneglycol-dimethylether, lower alkyl acetates, preferaby methyl- or ethyl-acetate, acetone, methylethylketone, and others. Particularly advantageous reaction media are, however, lower alcohols having 1 to 4 carbon atoms, especially methanol, ethanol and isopropanol. Mixtures of the above-mentioned solvents may also be used. The reactants may be present in the solvent in a suspended or dissolved form. The reactants may also be reacted without using a solvent, but in these cases side-reactions may occur due to the exothermic course, so that this process variant does not bring any advantages as compared with the method of operation in solvents. The reaction proceeds in a moderately exothermic manner and can be carried out at a temperature of from $-40°$ to $+100°$ C., preferably between 10° and 70° C. A temperature range of from 15° to 40° C. has proved particularly advantageous.

The reaction time depends largely on the reaction temperature applied and is between 2 minutes and 48 hours. In the most favorable temperature range, the reaction time is generally between 10 minutes and 8 hours.

As on the one hand the compounds of the formula III are preferably reacted in the form of salt-like compounds with the ketone II leading to the formation of salts MX, wherein M and X have the meanings given above, and on the other hand the reaction of II with III proceeds generally in a quantitative manner, the individual methods of working-up result in a separation of the compounds of the inventon from salt-like accompanying substances.

The said separation may be effected in a manner that the salt-like products are precipitated by means of a precipitant, then centrifuged or filtered off, and the desired compounds are isolated by carefully evaporating the solvent. Considering the different dissolving properties of the reaction products, the working-up is preferably effected in a manner that — optionally after previous concentration — the reaction mixture is mixed with water, and the thiazolidine derivatives (I) are thus separated, whereas the salt-like accomanying substances remain in the solution. The compounds I obtained as solid matter are either filtered off or are extracted with an appropriate solvent, especially methyl or ethyl acetate, and then obtained by a mild evaporation of the extract. As the reactant III is in many cases present in the form of an auto-oxidizable substance, the working under $N_2$ during the reaction and precipitation often leads to optimum yields.

The thiocarbamic acid derivatives of the formula III used are salts which have partially been described in the literature. The known compounds, as well as those not yet described, may be prepared according to methods known in the literature [Houben-Weyl, "Methoden der Org. Chemie", IVth edition, 1955, Vol. IX, page 823; Arch. Pharm. 293, 957 (1960)].

Compounds of the formula III are advantageously prepared from an amine $R^1$—$NH_2$ and carbon disulfide ($Z=S$) or carbon oxisulfide ($Z=O$), in which case either 2 mole equivalents of the amine $R^1$—$NH_2$ or 1 mole equivalent of the amine $R^1$—$NH_2$ in the presence of an organic or inorganic auxiliary base is reacted with one equivalent of carbon disulfide or oxysulfide. In the former case, thiocarbamates of the formula III wherein $M^\oplus$ is $R^1$— $NH_3^\oplus$ are obtained, and with the use of an organic auxiliary base, for example a tertiary amine $R_3N$, those wherein $M^\oplus$ is $HNR_3^\oplus$ are formed. With the use of an inorganic base, for example a metal hydroxide MOH, M stands preferably for $Na^+$ and $K^+$.

In the compounds of the formula II, there may be used as the radical of an activated ester Z, for example, Cl, Br, I, $CH_3$—$SO_2$—O—, $C_2H_5$ —$SO_2$—O—, $C_6H_5$—$SO_2$—O—, or $CH_3C_6H_4$—$SO_2$—O—. They can be obtained by several methods.

In this way, the diazo-ketones of the general formula XI

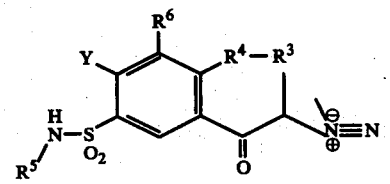

may be converted with acids into the ketones of the formula II, in which $R^3$ to $R^6$ and Y are defined as above and $R^2$ stands for H. This process as well as a number of compound of the formulae II and XI are known (Swiss Patent Specification No. 389,591 and Belgian Patent Specification No. 610,633). The other compounds of formulae II and XI may be prepared and reacted accordingly.

Since diazoalkanes are extremely poisonous, explosive and difficult to manipulate. The compounds of the formula II, in which $R^2$ to $R^6$ and Y are defined as above and Z stands for chlorine or bromine, are prepared in a more advantageous manner by reacting compounds of the general formula XII

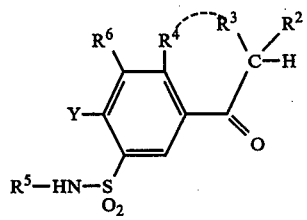

XII with a suitable halogenating agent, for example with elementary chlorine or bromine, sulfuryl chloride, monochlorourea, copper-II-bromide, bromodioxan or N-bromosuccinimide under the conditions known from the literature. The compounds of the formula XII, which are easily accessible, wherein Y stands for chlorine, $R^3$ stands for hydrogen, methyl and ethyl, and $R^4$ and $R^5$ stand for hydrogen are known (Arzneimittel-Forsch. 13, 269 (1963)). The other compounds of the formula XII which are required for the process of the invention are prepared in an analogous manner.

Finally, the compounds of the formula II may also be obtained by reacting under conditions known from the literature the α-hydroxyketones of the formula XIII

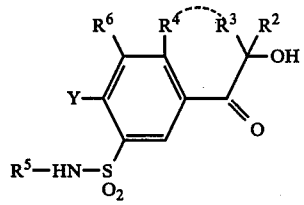

XIII known from Swiss Patent Specification No. 389,591 or compounds accordingly substituted, which may be prepared in an analogous manner, with the activated derivatives of organic and inorganic acids, such as methanesulfonic acid-chloride, ethane-sulfonic acid-chloride, benzene-sulfonic acid-chloride, p-toluene-sulfonic acid-chloride, thionyl bromide, phosphorus trichloride, phosphorus tribromide, phosphorus oxide chloride, thionyl chloride.

According to the method mentioned under (b) above, halogeno-ketones of the formula IV are reacted with thiocarbamidates of the general formula III, in which process the reactants are reacted suitably in an approximately equimolar ratio. The reaction conditions (temperature, time, solvent) correspond virtually to those specified in method (a) above, alcohols, however not being particularly suitable as reaction media in this case. The intermediate products of formula V formed in this process can be obtained by evaporating the solvent under reduced pressure any by treating the residue subsequently with water or in water-soluble solvents, such as alcohols, DMF or diethylene-glycol-dimethylether, by adding water.

However, the sulfonic acid chlorides of the formula V are preferably reacted without isolation or purification with ammonia or an amine of the formula VI to give compounds of the formula I. It is possible to use aqueous solutions of ammonia as well as of the amines VI and also liquid ammonia or pure amines in an excess amount, with the excess ammonia or amine acting as solvent at the same time. The reaction may also be carried out in organic solvents, such as lower alcohols, dimethylformamide, dimethylacetamide, dimethylsulfoxide, dioxan, tetrahydrofuran or diethylene-glycol-dimethylether. Lower alcohols having 1 to 4 carbon atoms are preferred. For the reaction of the sulfochlorides V to give the sulfonamides I, 1 mole equivalent of ammonia and/or amine VI in the presence of 1 mole equivalent of an auxiliary base are required. Per mole of sulfochloride V, at least 2 moles of ammonia or amine VI are therefore used.

It is also possible to operate with 1 mole of ammonia or amine VI, if the operation is carried out in the presence of an auxiliary base, using about 1 to 3 molar equivalents of auxiliary base. As auxiliary bases, inorganic and organic bases, such as inorganic hydroxides, carbonates and bicarbonates, as well as salt solutions of weak inorganic and organic acids, tertiary amines, such as triethylamine, tri-n-butylamine, methyl-dicyclohexylamine and ethyl-dicylohexylamine being particularly advantageous. The tertiary amine may likewise serve, if used in an excess amount, as reaction medium. The reaction proceeds exothermically, and it is of advantage to cool and to work at temperatures in the range of from −35° to +60° C., preferably from +10° to +35° C. The reaction time should be at least 30 minutes, and the reaction can be discontinued after 2 days at the latest, since longer reaction times do not bring any essential advantages. A reaction time of 6 to 20 hours is preferred. The working-up is advantageously carried out — optionally after removal by distillation of the amine and concentration — by diluting the reaction mixture with water, in which process compounds of the formula I precipitate in a sparingly soluble form. The aqueous precipitation medium should have a pH value of less than 8.

Directly after the precipitation with water, compounds of the formula I separate in the form of viscous oils in most cases. The crystallization can be accelerated by several treatments with a suitable solvent, for example water, ether, diisopropyl-ether, carbon tetrachloride, petroleum ether, n-butyl-acetate, etc.

After the precipitation with water, compounds of the formula I can also be extracted, in a manner analogous to that of method a) above, with a suitable solvent, preferably methyl or ethyl acetate. After drying the extract over a drying agent, such as sodium or magnesium sulfate, compounds of the formula I are obtained preferably by evaporation of the solution under reduced pressure.

The compounds of the formula IV used as starting compounds are obtained from the sulfonic acid halides of the formula XIV

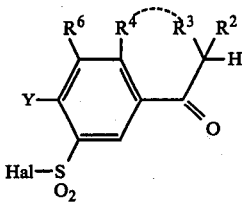

XIV by a reaction with a halogenating agent, the reaction conditions, solvents and halogenating agents corresponding to those of the corresponding reaction under method a) above. The compounds of the general formula XIV are partially known and also serve as starting compounds for the sulfonamides having the general formula XII.

The sulfochlorides XIV are preferably obtained from compounds XV

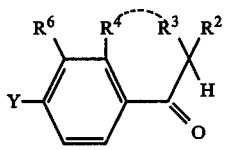

XV in known manner by nitration, reduction and subsequent Meerwein reaction.

According to method (c), compounds of the formula VII are reacted in a solvent with the known compounds of the formula VIII. As solvents, lower alcohols with 1 to 4 carbon atoms as well as methyl or ethyl acetate are particularly suitable.

The reaction is generally carried out in a temperature range of from 0° to 60° C., preferably from 15° to 35° C., the reaction time being between 5 and 60 hours.

For carrying out method (d), the mercapto-ketones of the formula VII are reacted in an anhydrous polar inert solvent, for example, dioxan, tetrahydrofuran, methyl acetate or ethyl acetate, with alkyl-isocyanates or alkyl-isothiocyanates of the formula IX in a molar ratio of 1:1.

The reactions may be carried out in a temperature range of from 0° to 40° C., preferably from 10° to 30° C., with the reaction time being between 1 and 20 hours.

The compounds of the formula VII used in methods (c) and (d) above may be obtained in different ways. For example, the compounds of the formula II can be converted with thiocarboxylic acids of the formula XVI

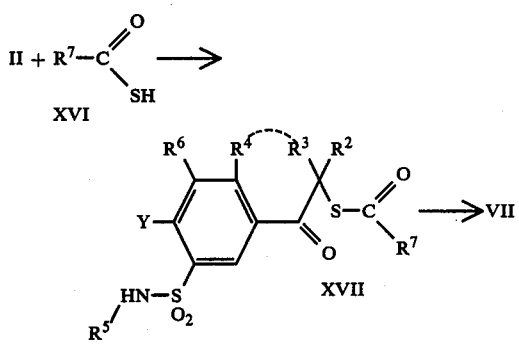

preferably with thio-acetic acid ($R^7 = CH_3$) in the presence of one equivalent of base, for example KOH, in an aqueous or alcoholic medium into the thio-esters of the general formula XVII which are hydrolyzed in a weakly alkaline medium to give the compounds of the formula VII. $R^7$ in formulae XVI and XVII represents a lower alkyl or aryl radical.

Compounds of the formula VII may also be prepared by reaction of compounds of the formula II with alkali metal hydrogeno-sulfides in an inert solvent, such as sodium or potassium bisulfide, in dimethylformamide at a temperature of from 0° to 40° C. The processes yielding compounds of the formula VII are known in literature.

According to method (e), the compounds of the general formula X are converted with the aid of a suitable oxidizing agent, preferably with active manganese-IV-oxide, into the compounds of the formula I. As solvents, there are used preferably halogenated hydrocarbons, for example, methylene chloride, chloroform, tetrachloroethane, the reaction being carried out at a temperature of from 0° to 40° C., preferably from 20° to 30° C., over a period of from 10 to 60 hours.

The compounds of the formula X are obtained by converting, for example, the halogeno-ketones of the formula II, in which X stands for chlorine or bromine, for example according to the method described in Arzneimittel-Forsch. 22, 2095 (1972), with an appropriate reducing agent, preferably with sodium-boronhydride in methanol at a temperature of from 0° to 25° C. into the compounds of the formula XVIII

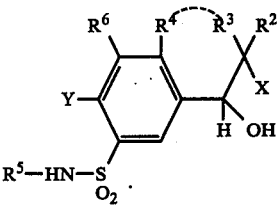

XVIII

As halogeno-alkyl derivatives, compounds of the formula XVIII react with the thiocarbamic acid derivatives of the formula III under the conditions as specified in method (a) above to form the compounds of the general formula X.

The most important compounds of the invention are those of the general formula I, in which the substituents have the following meanings:
$R^1$: Methyl, ethyl
$R^2$: hydrogen, methyl
$R^3$: hydrogen, methyl
$R^4$, $R^5$, $R^6$: hydrogen
as well as $R^3$ and $R^4$ together alkylene
Y: chlorine, bromine
Z: oxygen, sulfur.

Furthermore, as preferred compounds there may be mentioned compounds of the formula I in which the substituents have the following meanings:
$R^1$: Isopropyl allyl
$R^2$: hydrogen
$R^3$: hydrogen, methyl, ethyl
$R^4$: hydrogen, halogen
as well as $R^3$, $R^4$ together alkylene
$R^5$: hydrogen, benzyl
$R^6$: hydrogen, chlorine
Y: chlorine, bromine
Z: oxygen, sulfur.

In addition to the 4-(3-sulfamoyl-phenyl)-1,3-thiazolidine-4-ols described in the Examples, there may also be prepared according to the invention, for example, the compounds of the general formula I listed in the following Table:

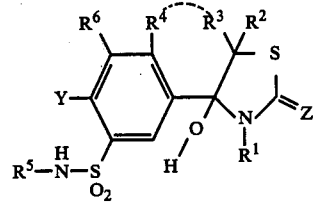

| | $R^1$ | $R^2$ | $R^3$ | $R^4$ | $R^5$ | $R^6$ | Y | Z |
|---|---|---|---|---|---|---|---|---|
| 1 | $CH_3$ | $CH_3$ | $CH_3$ | H | H | H | Cl | O |
| 2 | $CH_3$ | $CH_3$ | $CH_3$ | H | H | H | Cl | S |
| 3 | $CH_3$ | H | $n-C_3H_7$ | H | H | H | Cl | O |
| 4 | $CH_3$ | H | $n-C_4H_9$ | H | H | H | Cl | O |
| 5 | $CH_3$ | H | $n-C_4H_9$ | H | H | H | Cl | S |
| 6 | $CH_3$ | H | $CH(CH_3)_2$ | H | H | H | Cl | O |
| 7 | $CH_3$ | H | $CH(CH_3)CH_2CH_3$ | H | H | H | Cl | O |
| 8 | $CH_3$ | H | $CH_2CH(CH_3)_2$ | H | H | H | Cl | O |
| 9 | $CH_3$ | H | $C(CH_3)_3$ | H | H | H | Cl | O |
| 10 | $CH_3$ | H | $CH_3$ | H | H | H | Br | O |
| 11 | $CH_3$ | H | $CH_3$ | H | H | H | Br | O |
| 12 | $CH_3$ | H | $C_2H_5$ | H | H | H | Br | O |
| 13 | $CH_3$ | H | $CH(CH_3)_2$ | H | H | H | Br | O |
| 14 | $CH_3$ | H | $n-C_4H_9$ | H | H | H | Br | O |
| 15 | $CH_3$ | H | $CH_3$ | Cl | H | H | Cl | O |
| 16 | $CH_3$ | H | $C_2H_5$ | Cl | H | H | Cl | O |
| 17 | $CH_3$ | H | H | Cl | $CH_2C_6H_5$ | H | Cl | O |
| 18 | $CH_3$ | H | $CH_3$ | Cl | H | H | Cl | S |
| 19 | $CH_3$ | H | $CH_3$ | H | H | Cl | Cl | O |
| 20 | $CH_3$ | H | $C_2H_5$ | H | H | Cl | Cl | O |
| 21 | $CH_3$ | H | $CH_3$ | H | H | Cl | Cl | S |
| 22 | $CH_3$ | H | $CH(CH_3)_2$ | H | H | Cl | Cl | O |
| 23 | $CH_3$ | H | H | H | $CH_2C_6H_5$ | Cl | Cl | O |
| 24 | $C_2H_5$ | H | H | H | H | Cl | Cl | O |
| 25 | $CH_3$ | H | H | H | H | Br | Cl | O |
| 26 | $CH_3$ | $C_2H_5$ | $-CH_2-$ | | H | H | Cl | O |
| 27 | $C_2H_5$ | $C_2H_5$ | $-CH_2-$ | | H | H | Cl | O |
| 28 | $CH_3$ | $-CH(CH_3)_2$ (as $-CH-$ with two $CH_3$) | $-CH_2-$ | | H | H | Cl | O |
| 29 | $CH_3$ | $CH(CH_3)_2$ | $-CH_2-$ | | H | H | Cl | S |
| 30 | $CH_3$ | $CH_2CH_2CH_3$ | $-CH_2-$ | | H | H | Cl | O |
| 31 | $C_2H_5$ | $CH_2-CH_2CH_3$ | $-CH_2-$ | | H | H | Cl | S |
| 32 | $CH_3$ | $CH_2CH_2CH_3$ | $-CH_2-$ | | H | H | Cl | S |
| 33 | $CH_3$ | H | $-CH(CH_3)-CH(CH_3)-$ | | H | H | Cl | O |
| 34 | $CH_3$ | H | $-CH(CH_3)-CH(CH_3)-$ | | H | H | Br | O |
| 35 | $CH_3$ | H | $-CH(CH_3)-CH(CH_3)-$ | | H | H | Cl | S |
| 36 | $C_2H_5$ | H | $-CH(CH_3)-CH(CH_3)-$ | | H | H | Cl | O |

-continued

| | $R^1$ | $R^2$ | $R^3$ | $R^4$ | $R^5$ | $R^6$ | Y | Z |
|---|---|---|---|---|---|---|---|---|
| 37 | $CH_3$ | H | | $\begin{array}{c}-CH-\\|\\C_2H_5\end{array}$ | H | H | Cl | O |
| 38 | $CH_3$ | $CH_3$ | | $\begin{array}{c}-CH-\\|\\CH_3\end{array}$ | H | H | Cl | O |
| 39 | $CH_3$ | H | | $\begin{array}{c}-CH-\\|\\CH_2-C_2H_5\end{array}$ | H | H | Cl | S |
| 40 | $C_2H_5$ | H | | $\begin{array}{c}-CH-\\|\\CH_2-C_2H_5\end{array}$ | H | H | Br | O |
| 41 | $CH_3$ | H | | $\begin{array}{c}-CH-\\|\\CH(CH_3)_2\end{array}$ | H | H | Cl | O |
| 42 | $CH_2=CH-CH_2$ | $C_2H_5$ | | $\begin{array}{c}-CH-\\|\\(CH_2)_3CH_3\end{array}$ | H | H | Cl | O |
| 43 | $CH_3$ | H | | $\begin{array}{c}-CH-\\|\\CH(CH_3)_2\end{array}$ | H | H | Cl | S |
| 44 | $CH_3$ | $CH(CH_3)_2$ | | $\begin{array}{c}-CH-\\|\\CH_2CH_3\end{array}$ | H | H | Cl | O |
| 45 | $CH_3$ | $CH_2-CH_2-CH_3$ | | $\begin{array}{c}-CH-\\|\\CH_3\end{array}$ | H | H | Cl | O |
| 46 | $CH_3$ | H | | $-(CH_2)_2-$ | H | H | Cl | O |
| 47 | $C_2H_5$ | H | | $-(CH_2)_2-$ | H | H | Cl | O |
| 48 | $CH_3$ | H | | $-(CH_2)_2-$ | H | H | Cl | S |
| 49 | $C_2H_5$ | H | | $-(CH_2)_2-$ | H | H | Br | O |
| 50 | $CH_3$ | H | | $\begin{array}{c}-CH_2-CH-\\|\\CH_3\end{array}$ | H | H | Cl | O |
| 51 | $CH_3$ | H | | $\begin{array}{c}-CH-CH_2-\\|\\CH_3\end{array}$ | H | H | Cl | O |
| 52 | $CH_3$ | H | | $-(CH_2)_3-$ | H | H | Cl | O |
| 53 | $CH_3$ | H | | $-(CH_2)_3-$ | H | H | Cl | S |
| 54 | $CH_3$ | H | | $-(CH_2)_3-$ | H | H | Br | O |
| 55 | $CH_3$ | H | | $-CH_2-$ | H | H | Br | O |
| 56 | $C_2H_5$ | H | | $-CH_2-$ | H | H | Br | O |
| 57 | $CH_3$ | H | | $-CH_2-$ | H | H | Br | S |
| 58 | $C_2H_5$ | $CH_3$ | | $-CH_2-$ | H | H | Br | S |
| 59 | $CH_3$ | $CH(CH_3)_2$ | | $-CH_2-$ | H | H | Br | O |
| 60 | $CH_3$ | $CH_3$ | | $-CH_2-$ | H | H | Br | O |
| 61 | $CH_3$ | $CH_3$ | | $\begin{array}{c}-CH-\\|\\CH_3\end{array}$ | H | H | Br | O |

The compounds of the invention are valuable medicaments and are distinguished by a very good diuretic and saluretic action.

In some patent specifications, an anorectic effect which stimulates the central nervous system as well as a diuretic action of 4-aryl-1,3-thiazolidine-4-ol-derivatives has been described (cf. German Offenlegungsschrift No. 1,938,674, U.S. Pat. No. 3,671,534), in which case the compounds mentioned are compounds without sulfonamide groups at the aromatic nucleus, the diuretic action of which depending to a high degree on a specific substitution of the thiazolidine ring. It was a surprising fact which could not have been foreseen that the novel compounds of the invention show a very strong salidiuretic effect due to the introduction of a sulfanamide group in the 3-position of the benzene nucleus, independent of this specific ring substitution, this effect being markedly superior to these known thiazolidine derivatives, with regard to quality and quantity. Moreover, the less desired anorectic active ingredient which stimulates the central nervous system has been largely suppressed.

The salidiuretic action of the novel compounds of the invention was determined on the rat with a unit dose of 50 mg/kg orally. It was found that this action was superior to the salidiuretic action of known commercial preparations of the thiazide group, for example the hydrochlorothiazide, and to that of chlorothalidone. In addition thereto, the novel compounds of the invention are distinguished by a long lasting action time which corresponding approximately to that of chlorothalidone. Therefore, the novel compounds of the invention are suitable in particular for the treatment of hypertonic conditions, in which case they will be combined with a usual antihypertonic agent.

Therapeutic compositions of the novel compounds are in particular tablets, dragées, capsules and suppositories as well as ampules for parenteral administration (i.v., s.c. and i.m.). The products of the invention are contained in these compositions preferably in the form of their acid addition salts. The therapeutical dosage unit is between 5 and 500 mg, preferably 10 to 100 mg per tablet.

In addition to the usual filler and carrier substances, these compositions may also contain an antihypertensive agent, especially if they are intended for the therapy of high blood pressure, for example reserpin, hydralazine, guanethidine, α-methyldopa or clonidine.

Moreover, therapeutical combination compositions with potassium-retaining compounds such as aldosterone-antagonists, for example spironolactone, or pseudo-aldosterone-antagonists such as Triamterene or Amiloride are of interest. Furthermore, the K+-substitution may also be made with the aid of various forms for administration, for example dragées, tablets, effervescent tablets, lotions, etc.

The following Examples illustrate the invention. In these examples, the melting and decomposition points are not corrected.

EXAMPLE 1

2-Bromo-5-chloro-6-sulfamoyl-1-indanone (a) 5-Chloro-6-nitro-1-indanone 540 ml of fuming nitric acid ($d=1.52$) are mixed portionwise at −20° C. with 86 g (0.51 mole) of 5 chloro-1-indanone. The reaction mixture is then stirred for 45 minutes at −15° to −20° C., then it is poured on ice and the precipitate is filtered off and washed with water.

The raw product (melting point 110° to 113° C.) yields after recrystallization from ethanol the pure substance having a melting point of 126° to 128° C.

(b) 5-Chloro-6-amino-1-indanone

114 Grams (2.01 moles) of iron powder are added to a solution of 134 g (0.64 mole) of 5-chloro-6-nitro-1-indanone in 1600 ml of ethanol, then 63.5 ml of concentrated hydrochloric acid are added dropwise, and the reaction mixture is boiled for 4 hours. The precipitate is filtered off with suction, and the product is precipitated from the hot filtrate by the addition of water, then suction-filtered and washed with water. The residue of the reaction mixture is boiled with chloroform, the filtrate is dried with $Na_2SO_4$ and is then concentrated to dryness, after which process a further amount of the product is obtained. The substance melts at a temperature of from 198° to 200° C., and after recyrstallization from ethanol the melting point is in the range of from 203° to 205° C.

(c) 5-Chloro-6-chlorosulfonyl-1-indanone

84 Grams (0.46 mole) of 5-chloro-6-amino-1-indanone are suspended in 1050 ml of semi-concentrated hydrochloric acid, and the mixture is diazotized at 0° C. with a solution of 32.6 g (0.46 mole) of sodium nitrite in 100 ml of water. Stirring of the mixture is continued to be stirred for 15 minutes, and the diazonium salt solution is introduced portionwise at 0° to 5° C. to a suspension of 39.9 g of $CuCl_2 .2 H_2O$ in 1250 ml of glacial acetic acid saturated with $SO_2$. The reaction mixture is allowed to reach room temperature, then it is stirred for another 30 minutes, in which process part of the reaction product precipitates, and the mixture is diluted with 1000 ml of water. It is then stirred again for 15 minutes, the precipitate is filtered off with suction and washed with water. The compound has a melting point in the range of from 136° to 138° C., and after recrystallization from ethyl acetate the melting point is 146° to 148° C.

(d) 5-Chloro-6-sulfamoyl-1-indanone 99.6 Grams of 5-chloro-6-chlorosulfonyl-1-indanone are introduced portionwise into 700 ml of liquid ammonia. The solvent is allowed to evaporate and the residue is dissolved in water, is heated within a short time on the water-bath and is filtered after the addition of active charcoal. The solution is acidified with hydrochloric acid to a pH of 2, the precipitate is filtered off with suction and is washed with water. The melting point of 5-chloro-6-sulfamoyl-1-indanone is in the range of from 205° to 208° C., and after recrystallization from a mixture of acetone and water it is 216° to 218° C.

(e) 2-Bromo-5-chloro-6-sulfamoyl-1-indanone 0.1 Milliliter of 48% aqueus HBr is added to a suspension of 52 g (0.21 mole) of 5-chloro-6-sulfamoyl-1-indanone in 530 ml of glacial acetic acid. Subsequently a solution of 34.0 g (0.21 mole) of bromine in 160 ml of glacial acetic acid is added dropwise. The mixture is stirred for another 1.5 hours, and is then poured into a solution of 4.5 g of $NaHSO_3$ in 2 of ice water. The 2-bromo-5-chloro-6sulfamoyl-1-indanone which crystallizes after stirring for some time is filtered off with suction and is washed with water.

By reprecipitating the same form a mixture of ethyl acetate and petroleum ether, the melting point of the compound rose from 174°–178° to 184°–186° C.

EXAMPLE 2

2-Bromo-5-chloro-6-n-propylsulfamoyl-1-indanone (a) 5-Chloro-6-n-propylsulfamoyl-1-indanone A solution of 1.95 g (33 mmoles) of n-propylamine and 3.04 g (30 mmoles) of triethylamine in 50 ml of acetone is added to a solution of 7.95 g (30 mmoles) of 5-chloro-6-chlorosulfonyl-1-indanone in 50 ml of acetone, and the whole is stirred for 6 hours at room temperature, thereafter for 1 hour at boiling temperature. The solution is largely concentrated, 200 ml of water are added, and the mixture is then acidified with 2N hydrochloric acid to a pH of 2. The precipitate is filtered off with suction and washed with water. The product melts at 122° to 123° C.

(b) 2-Bromo-5-chloro-6-n-propylsulfamoyl-1-indanone 0.5 L Milliliter of 48% aqueous HBr is added to a solution of 5.76 g (20 mmoles) of 5-chloro-6-n-propylsulfamoyl-1-indanone in 50 ml of ethyl acetate. Thereafter a solution of 3.20 g (20 mmoles) of bromine in 20 ml of ethyl acetate is added dropwise. The mixture is stirred for 1 hour at room temperature, then the solution is concentrated to dryness, and 50 ml of water are added to the residue. The crystalline precipitate is filtered off with suction and washed with water. 2-Bromo-5-chloro-6-n-propylsulfamoyl-1-indanone is obtained which has a melting point of from 150° to 154° C.

EXAMPLE 3

6-Benzylsulfamoyl-2-bromo-5-chloro-1-indanone (a) 6-Benzylsulfamoyl-5-chloro-1-indanone According to Example 2(a), 13.26 g (50 mmoles) of 5-chloro-6-chlorosulfonyl-1-indanone, 5.89 g (55 mmoles) of benzylamine and 5.05 g (50 mmoes) of triethylamine in a total of 100 ml of acetone yield 6-benzylsulfamoyl-5-chloro-1-indanone having a melting point of 203° to 205° C., from which the pure product is obtained after a recrystallization from ethanol, said product having a melting point of 228° to 231° C.

(b) 6-Benzylsulfamoyl-2-bromo-5-chloro-1-indanone

According to Example 1 e), 10.05 g (30 mmoles) of 6-benzylsulfamoyl-5-chloro-1-indanone and 4.8 g (30 mmoles) of bromine in a total of 110 ml of glacial acetic acid yield the substance having a melting point of from 159° to 161° C. which after reprecipitation from a mixture of ethyl acetate and petroleum ether has a melting point in the range of from 176° to 178° C.

EXAMPLE 4

2-Bromo-5-chloro-2-methyl-6-sulfamoyl-1-indanone (a) 5-Chloro-2-methyl-6-nitro-1-indanone According to Example 1 (a), 28.0 g (0.155 mole) of 5-chloro-2-methyl-1-indanone and 180 ml of fuming nitric acid yield the nitro compound having a melting point of from 75° to 78° C., which after recrystallization from ethanol rises to 87° to 89° C.

(b) 6-Amino-5-chloro-2-methyl-1-indanone 13.6 Milliliters of concentrated hydrochloric acid are added dropwise to a mixture of 30.7 g (0.136 mole) of 5-chloro-2-methyl-6-nitro-1-indanone and 24.55 g of iron powder in 340 ml of ethanol, and the suspension is boiled for 4 hours. The mixture is filtered off with suction from the precipitate in a hot state, after which process the compound precipitates partially from the filtrate when cooling. After having distilled off the solvent to a large extent, the precipitate is completed by diluting with water.

The product is filtered off with suction and washed with water. Its melting point is from 135° to 138° C.

(c) 5-Chloro-6-chlorosulfonyl-2-methyl-1-indanone

According to Example 1 (c), 5-chloro-6-chlorosulfonyl-2-methyl-1-indanone having a melting point of from 107° to 111° C. is obtained from 17.3 g (0.084 mole) of 6-amino-5-chloro-2-methyl-1-indanone after diazotization with 6.23 g (0.0884 mole) of sodium nitrite in 30 ml of water and introduction of the diazonium salt solution into a suspension of 7.63 g (0.045 mole) of $CuCl_2.2 H_2O$ in 240 ml of glacial acetic acid saturated with $SO_2$.

(d) 5-Chloro-2-methyl-6-sulfamoyl-1-indanone

According to Example 1 (d), the reaction of 5-chloro-6-chlorosulfonyl-2-methyl-1-indanone with liquid ammonia yields the raw product having a melting point of from 180° to 184° C. After recrystallization from ethanol, the compound melts at 190° to 192° C.

(e) 2-Bromo-5-chloro-2-methyl-6-sulfamoyl-1-indanone

According to Example 1 (e), 9.7 g (0.037 mole) of 5-chloro-2-methyl-6-sulfamoyl-1-indanone and 5.97 g (0.037 mole) of bromine in a total of 95 ml of glacial acetic acid yield 2-bromo-5-chloro-2-methyl-6-sulfamoyl-1-indanone, which melts at a temperature of from 136° to 138° C. after reprecipitation from a mixture of ethyl acetate and petroleum ether.

EXAMPLE 5

6-Chloro-3a-hydroxy-3-methyl-5-sulfamoyl-8H-indeno-[2,1-b]-thiazolidine-2-thione A solution of 1.48 g (10 mmoles) of methylammonium-N-methyldithiocarbamate is added to a solution of 3.26 g (10 mmoles) of 2-bromo-5-chloro-6-sulfamoyl-1-indanone in 30 ml of ethanol under a nitrogen atmosphere, and the mixture is stirred for 5 hours at room temperature. The solution is concentrated to a third of its volume, then 250 to 300 ml of water are added portionwise, and the suspension obtained is stirred for some time until the crystallization is completed. The crystalline precipitate is filtered off with suction and washed with water. The reaction product melts at 198° to 202° C. (decomposition).

EXAMPLE 6

3-Ethyl-6-chloro-3a-hydroxy-5-sulfamoyl-8H-indeno-[2,1-b]-thiazolidine-2-thione According to Example 5, 3.26 g (10 mmoles) of 2-bromo-5-chloro-6-sulfamoyl-1-indanone and 1.66 g (10 mmoles) of ethylammonium-N-ethyl-dithiocarbamate yield 3-ethyl-6-chloro-3a-hydroxy-5-sulfamoyl-8H-indeno-[2,1-b]-thiazolidine-2-thione (melting point 288° to 290° C. under decomposition).

EXAMPLE 7

6-Chloro-3a-hydroxy-3-methyl-5-sulfamoyl-8H-indeno-[2,1-b]-thiazolidine-2-one According to Example 5, the substance mentioned above is prepared from 4.89 g (15 mmoles) of 2-bromo-5-chloro-6-sulfamoyl-1-indanone and 3.34 g (22.5 mmoles) of methylammonium-N-methylthiocarbamate and is then stirred with acetonitrile. After filtration and concentration of the filtrate, the pure product is obtained (decomposition point 141° to 144° C.).

EXAMPLE 8

3-Ethyl-6-chloro-3a-hydroxy-5-sulfamoyl-8H-indeno-[2,1-b]-thiazolidine-2-one By reacting 3.26 g (10 mmoles) of 2-bromo-5-chloro-6-sulfamoyl-1-indanone with 2.25 g (15 mmoles) of ethylammonium-N-ethyl-thiocarbamate according to Example 5, 3-ethyl-6-chloro-3a-hydroxy-5-sulfamoyl-8H-indeno-[2,1-b]-thiazolidine-2-one is obtained (decomposition point 170° to 172° C.).

EXAMPLE 9

6-Chloro-3a-hydroxy-3-n-propyl-5-sulfamoyl-8H-indeno-[2,1-b]-thiazolidine-2-thione According to Example 5, the reaction product having a decomposition point of from 236° to 240° C. is obtained from 3.26 g (10 mmoles) of 2-bromo-5-chloro-6-sulfamoyl-1-indanone and 4.20 g (15 mmoles) of n-propylammonium-N-n-propyl-dithiocarbamate.

EXAMPLE 10

6-Chloro-3a-hydroxy-3-isopropyl-5-sulfamoyl-8H-indeno-[2,1-b]-thiazolidine-2-thione According to Example 5, 4.89 g (15 mmoles) of 2-bromo-5-chloro-6-sulfamoyl-1-indanone and 3.65 g (15 mmoles) of isopropylammonium-N-isopropyl-dithiocarbamate yield the reaction product having a decomposition point of from 199° to 200° C.

EXAMPLE 11

3-Allyl-6-chloro-3a-hydroxy-5-sulfamoyl-8H-indeno-[2,1-b]-thiazolidine-2-thione According to Example 5, 3-allyl-6-chloro-3a-hydroxy-5-sulfamoyl-8H-indeno-[2,1-b]-thiazolidine-2-thione is obtained from 13.04 g (40 mmoles) of 2-bromo-5-chloro-6-sulfamoyl-1-indanone and 9.36 g (40 mmoles) of triethylammonium-N-allyldithiocarbamate (decomposition point 172° to 175° C.).

EXAMPLE 12

6-Chloro-3a-hydroxy-3-(3-pyridyl)-methyl-5-sulfamoyl-8H-indeno-[2,1-b]-thiazolidine-2-thione The reaction of 4.89 g (15 mmoles) of 2-bromo-5-chloro-6-sulfamoyl-1-indanone and 4.28 g of triethylammonium-N-3-pyridyl-methyl-dithiocarbamate according to Example 5 yields the reaction product (decomposition point 128° to 134° C.).

EXAMPLE 13

6-Chloro-3a-hydroxy-3,9-dimethyl-5-sulfamoyl-8H-indeno-[2,1-b]-thiazolidine-2-thione According to Example 7, 3.39 g (10 mmoles) of 2-bromo-5-chloro-2-methyl-6-sulfamoyl-1-indanone and 1.48 g (10 mmoles) of methylammonium-N-methyl-dithiocarbamate yield the above compound (decomposition point 155° to 160° C.).

EXAMPLE 14

6-Chloro-3a-hydroxy-3,9-dimethyl-5-sulfamoyl-8H-indeno-[2,1-b]-thiazolidine-2-one According to Example 5, the above compound is prepared from 3.39 g (10 mmoles) of 2-bromo-5-chloro-2-methyl-6-sulfamoyl-1-indanone and 1.8 g (15 mmoles) of methylammonium-N-methylthiocarbamate, which compound is then stirred with acetonitrile. After filtration, the filtrate is concentrated, the residue is suspended with water, the crystalline precipitate is filtered off with suction and washed with water. The pure substance is obtained (decomposition point 150° to 154° C.).

EXAMPLE 15

6-Chloro-3a-hydroxy-3-isopropyl-5-sulfamoyl-8H-indeno-[2,1-b]-thiazolidine-2-one According to Example 14, 4.89 g (15 mmoles) of 2-bromo-5-chloro-6-sulfamoyl-1-indanone and 3.97 g (22.5 mmoles) of isopropylammonium-N-isopropyl-thiocarbamate yield the substance (decomposition point 145° to 148° C.).

EXAMPLE 16

6-Chloro-3a-hydroxy-3-(3-pyridyl)-methyl-5-sulfamoyl-8H-indeno-[2,1-b]-thiazolidine-2-one According to Example 14, the reaction of 3.26 g (10 mmoles) of 2-bromo-5-chloro-6-sulfamoyl-1-indanone and 2.74 g (10 mmoles) of 3-pyridylmethyl-ammonium-N-(3-pyridyl)-methylthiocarbamate yields the reaction product (decomposition point 112° to 115° C.).

EXAMPLE 17

3-Allyl-6-chloro-3a-hydroxy-5-sulfamoyl-8H-indeno-[2,1-b]-thiazolidine-2-one

According to Example 14, 3-allyl-6-chloro-3a-hydroxy-5-sulfamoyl-8H-indeno-[2,1-b]-thiazolidine-2-one is obtained from 9.78 g (30 mmoles) of 2-bromo-5-chloro-6-sulfamoyl-1-indanone and 7.75 g (45 mmoles) of allylammonium-N-allylthiocarbamate (decomposition point 122° to 125° C.).

EXAMPLE 18

5-Benzylsulfamoyl-6-chloro-3a-hydroxy-3-methyl-8H-indeno-[2,1-b]-thiazolidine-2-thione The reaction of 4.15 g (10 mmoles) of 6-benzylsulfamoyl-2-bromo-5-chloro-1-indanone with 1.48 g (10 mmoles) of methylammonium-N-methyl-dithiocarbamate according to Example 5 yields the above compound (decomposition point 148° to 150° C.).

EXAMPLE 19

3-Ethyl-5-benzylsulfamoyl-6-chloro-3a-hydroxy-8H-indeno-[2,1-b]-thiazolidine-2-thione According to Example 5, 4.15 g (10 mmoles) of 6-benzylsulfamoyl-2-bromo-5-chloro-1-indanone and 1.66 g (10 mmoles) of ethylammonium-N-ethyl-thiocarbamate yield the reaction product (decomposition point 130° to 132° C.).

EXAMPLE 20

3-Methyl-6-chloro-3a-hydroxy-5-n-propylsulfamoyl-8H-indeno-[2,1-b]-thiazolidine-2-thione According to Example 5, 3.67 g (10 mmoles) of 2-bromo-5-chloro-6-n-propylsulfamoyl-1-indanone and 1.48 g (10 mmoles) of methylammonium-N-methyl-dithiocarbamate yield the above compound (decomposition point 149° to 154° C.).

EXAMPLE 21

3-Ethyl-6-chloro-3a-hydroxy-5-n-propylsulfamoyl-8H-indeno-[2,1-b]-thiazolidine-2-thione According to Example 5, from 1.84 g (5 mmoles) of 2-bromo-5-chloro-6-n-propylsulfamoyl-1-indanone and ethylammonium-N-ethyl-dithiocarbamate the above compound is prepared (decomposition point 112° to 115° C.).

EXAMPLE 22

6-Chloro-3a-hydroxy-3-(4-pyridyl)-methyl-5-sulfamoyl-8H-indeno-[2,1-b]-thiazolidine-2-thione According to Example 5, the reaction product which has a decomposition point of from 182° to 186° C. is obtained from 4.89 g (15 mmoles) of 2-bromo-5-chloro-6-sulfamoyl-1-indanone and 4.28 g of triethylammonium-N-(4-pyridyl)-methyldithiocarbamate.

EXAMPLE 23

4-(4-Chloro-3-sulfamoyl-phenyl)-3-methyl-2-thiazolidone-4-ol 1.22 Grams (0.01 mole) of methylammonium-N-methylthiocarbamate are introduced into 30 ml of ethanol under nitrogen protection, and 3.13 g (0.01 mole) of 2-bromo-4'-chloro-3'-sulfamoyl-acetophenone are added portionwise, while stirring thoroughly. The stirring is continued for 24 hours at room temperature, and afterwards 50 ml of water are introduced to complete the precipitation. Colorless crystals with a melting point of 182° C. are obtained (decomposition).

EXAMPLE 24

4-(4-Chloro-3-sulfamoyl-phenyl)-3-methyl-2-thiazolidine-thione-4-ol 1.38 g (0.01 mole) of methylammonium-N-methyl-dithiocarbamate are reacted with 3.13 g (0.01 mole) of 2-bromo-4'-chloro-3'-sulfamoyl-acetophenone in 30 ml of methanol according to Example 23 and are worked up. Melting point: 217° C. (decomposition).

EXAMPLE 25

3-Ethyl-4-(4-chloro-3-sulfamoyl-phenyl)-2-thiazolidone-4-ol 1.5 Grams (0.01 mole) of ethylammonium-N-ethyl-thiocarbamate are introduced into 30 ml of ethanol under a nitrogen atmosphere, and 3.13 g (0.01 mole) of 2-bromo-4'-chloro-3'-sulfamoyl-acetophenone are added portionwise, while stirring. The stirring is continued for 24 hours at room temperature, the solvent is distilled off in vacuo, in which process the external temperature should not exceed 40° C., if possible, and the residue is brought to crystallization under 50 ml of water at room temperature. Melting point: 189° C. (from acetonitrile).

EXAMPLE 26

4-(4-Chloro-3-methylsulfamoyl-phenyl)-3-methyl-2-thiazolidone-4-ol is obtained according to Example 25 from 2-bromo-4'-chloro-3'-methylsulfamoyl-acetophenone and methylammonium-N-methyl-thiocarbamate.
Melting point: 176° C.

EXAMPLE 27

4-(4-Chloro-3-propylsulfamoyl-phenyl)-3-methyl2-thiazolidone-4-ol is obtained according to Example 25 from 2-bromo-4'-chloro-3'-propylsulfamoyl-acetophenone and methylammonium-N-methyl-thiocarbamate.
Melting point: 184° C. (decomposition).

EXAMPLE 28

4-(4-Chloro-3-sulfamoyl-phenyl)-3-isobutyl-2-thiazolidine-thione-4-ol 2.22 Grams (0.01 mole) of isobutylammonium-N-isobutyl-dithiocarbamate are introduced into 30 ml of methanol under a nitrogen atmosphere, and 3.13 g (0.01 mole) of 2-bromo-4'-chloro-3'-sulfamoyl-acetophenone are added portionwise, while stirring. The mixture is stirred over night at room temperature, and the solvent is then distilled off in vacuo, at an external temperature not exceeding 40° C. The residue is mixed with 50 ml of water and is extracted twice with 40 ml of ethyl acetate each time. After separation and drying of the organic phase over sodium sulfate, the solvent is distilled off at a bath temperature of less than 40° C., and the residue is brought to crystallization under 10 to 20 ml of water.
Melting point: 131° C. (decomposition).

EXAMPLE 29

4-(4-Chloro-3-sulfamoyl-phenyl)-b 3-sec.butyl-2-thiazolidine-thione-4-ol is obtained according to Example 28 from 2-bromo-4'-chloro-3'-sulfamoyl-acetophenone and sec.-butylammonium-N-sec.butyl-dithiocarbamate.
Decomposition point: 175° C.

EXAMPLE 30

4-(4-Chloro-3-sulfamoyl-phenyl)-3-propyl-2-thiazolidine-thione-4-ol is obtained according to Example 28 from 2-bromo-4'-chloro-3'-sulfamoyl-acetophenone and propylammonium-N-propyl-dithiocarbamate.
Melting point: 129° to 131° C. (decomposition).

EXAMPLE 31

3-Allyl-4-(4-chloro-3-sulfamoyl-phenyl)-2-thiazolidine-thione-4-ol 1.9 Grams (0.01 mole) of allylammonium-N-allyl-dithiocarbamate are introduced into 30 ml of methanol under a nitrogen atmosphere, 3.13 g (0.01 mole) of 2-bromo-4'-chloro-3'-sulfamoyl-acetophenone are added portionwise, while stirring; then the reaction is continued according to Example 25.
The melting point is 148° C., decomposition starting at 162° C.

EXAMPLE 32

3,5-Diethyl-4-(4-chloro-3-sulfamoyl-phenyl)-2-thiazolidone-4-ol 1.5 Grams (0.01 mole) of ethylammonium-N-ethyl-thiocarbamate are dissolved in 35 ml of ethanol under a nitrogen atmosphere, 3.4 g (0.01 mole) of 2-bromo-4'-chloro-3'-sulfamoyl-butyrophenone are added portionwise, while stirring, and the reaction mixture is worked up according to Example 28.
Melting point: 137° C. (decomposition).

EXAMPLE 33

4-(4-Chloro-3-sulfamoyl-phenyl)-3-isopropyl-2-thiazolidine-thione-4-ol 1.94 Grams (0.01 mole) of isopropylammonium-N-isopropyl-dithiocarbamate are introduced into 50 ml of methanol under a nitrogen atmosphere and are then mixed portionwise with 2.67 g (0.01 mole) of 2,4'-dichloro-3'-sulfamoyl-acetophenone, while stirring, the stirring being continued for 10 minutes at room temperature, for 5 minutes at 45° C. and for another 3 hours at room temperature. The homogeneous reaction mixture is then filtered into 250 ml of water being stirred, the solvent is decanted off from the semi-crystalline precipitate, and the substance is brought to crystallization under 50 to 100 ml of water by stirring and trituration.
Melting point: 105° C. (decomposition).

EXAMPLE 34

3-Butyl-4-(4-chloro-3-sulfamoyl-phenyl)-2-thiazolidine-thione-4-ol is obtained according to Example 33 from 2,4'-dichloro-3'-sulfamoyl-acetophenone and sodium-N-butyldithiocarbamate.
Decomposition point: 98° C.

EXAMPLE 35

4-(4-Chloro-3-sulfamoyl-phenyl)-3-(2-pyridylmethyl)-2-thiazolidine-thione-4-ol is obtained according to Example 24 from 2-bromo-4'-chloro-3'-sulfamoyl-acetophenone and triethylammonium-N-(2-pyridylmethyl)-dithiocarbamate. Melting point: 113° C. (decomposition).

EXAMPLE 36

4-(4-Chloro-3-sulfamoyl-phenyl)-3-(3-pyridylmethyl)-2-thiazolidine-thione-4-ol is obtained according to Example 24 from 2-bromo-4'-chloro-3'-sulfamoyl-acetophenone and triethylammonium-N-(3-pyridylmethyl)-dithiocarbamate. Melting point: 163° C. (decomposition).

EXAMPLE 37

4-(4-Chloro-3-sulfamoyl-phenyl)-3-(2-pyridylmethyl)-2-thiazolidone-4-ol is obtained according to Example 24 from 2-bromo-4'-chloro-3'-sulfamoyl-acetophenone and triethylammonium-N-(2-pyridyl-methyl)-thiocarbamate. Melting point: 164° C. (decomposition).

EXAMPLE 38

4-(4-Chloro-3-sulfamoyl-phenyl)-3-propyl-2-thiazolidone-4-ol is obtained according to Example 31 from propylammonium-N-propyl-thiocarbamate and 2-bromo-4'-chloro-3'-sulfamoyl-acetophenone. Decomposition point: 131° C.

EXAMPLE 39

4-(4-Chloro-3-sulfamoyl-phenyl)-3,5-dimethyl-2-thiazolidine-thione-4-ol is obtained according to Example 31 from 2-bromo-4'-chloro-3'-sulfamoyl-propiophenone and methylammonium-N-methyl-dithiocarbamate. Melting point: 197° C. (decomposition).

EXAMPLE 40

5-Ethyl-4-(4-chloro-3-sulfamoyl-phenyl)-3-methyl-2-thiazolidine-thione-4-ol is obtained according to Example 31 from 2-bromo-4'-chloro-3'-sulfamoyl-butyrophenone and methylammonium-N-methyl-dithiocarbamate. Melting point: 162° C. (decomposition).

EXAMPLE 41

4-(4-Chloro-3-methylsulfamoyl-phenyl)-3-methyl-2-thiazolidine-thione-4-ol is obtained according to Example 31 from 2-bromo-4'-chloro-3'-methylsulfamoyl-acetophenone and methylammonium-N-methyl-dithiocarbamate. Melting point: 96° C.

EXAMPLE 42

4-(3-Ethylsulfamoyl-4-chlorophenyl)-3-methyl-2-thiazolidine-thione-4-ol is obtained according to Example 31 from 3'-ethylsulfamoyl-2-bromo-4'-chloro-acetophenone and methylammonium-N-methyl-dithiocarbamate. Melting point: 150° C. (decomposition).

EXAMPLE 43

4-(4-Bromo-3-sulfamoyl-phenyl)-3-methyl-2-thiazolidine-thione-4-ol is obtained according to Example 31 from 2,4'-dibromo-3'-sulfamoyl-acetophenone and methylammonium-N-methyl-dithiocarbamate.
Melting point 191° C. (decomposition).

EXAMPLE 44

3-Ethyl-4-(4-chloro-3-sulfamoyl-phenyl)-2-thiazolidine-thione-4-ol is obtained according to Example 31 from ethylammonium-N-ethyl-dithiocarbamate and 2-bromo-4'-chloro-3'-sulfamoyl-acetophenone. Melting point 170° C. (decomposition).

EXAMPLE 45

3-Ethyl-4-(4-chloro-3-sulfamoyl-phenyl)-5-methyl-2-thiazolidine-thione-4-ol is obtained according to Example 31 from 2-bromo-4'-chloro-3'-sulfamoyl-propiophenone and ethylammonium-N-ethyl-dithiocarbamate. Melting point 150° to 152° C. (decomposition).

EXAMPLE 46

4-(3-Benzylsulfamoyl-4-chloro-phenyl)-3-methyl-2-thiazolidine-thione-4-ol is obtained according to Example 31 from 3'-benzylsulfamoyl-2-bromo-4'-chloro-acetophenone and methylammonium-N-methyl-dithiocarbamate. Melting point 130° C. (decomposition).

EXAMPLE 47

4-(4-Chloro-3-sulfamoyl-phenyl)-3-isopropyl-2-thiazolidone-4-ol is obtained according to Example 31 from 2-bromo-4'-chloro-3'-sulfamoyl-acetophenone and isopropylammonium-N-isopropyl-thiocarbamate.
Amorphous solid matter is obtained, decomposition starting at 83° C.

EXAMPLE 48

4-(4-Chloro-3-sulfamoyl-phenyl)-3-(3-pyridylmethyl)-2-thiazolidone-4-ol is obtained according to Example 31 from 2-bromo-4'-chloro-3'-sulfamoyl-acetophenone and 3-pyridylmethyl-ammonium-N-3-pyridyl-methyl-thiocarbamate. Melting point: 148° C. (decomposition).

EXAMPLE 49

3-Ethyl-4-(4-chloro-3-sulfamoyl-phenyl)-5-methyl-2-thiazolidone-4-ol is obtained according to Example 28 from 2-bromo-4'-chloro-3'-sulfamoyl-propiophenone and ethylammonium-N-ethylthiocarbamate. Melting point: 178° C.

EXAMPLE 50

3-Allyl-4-(4-chloro-3-sulfamoyl-phenyl)-5-methyl-2-thiazolidone-4-ol is obtained according to Example 28 from 2-bromo-4'-chloro-3'-sulfamoyl-propiophenone and allylammonium-N-allyl-thiocarbamate. Decomposition point: 148° C.

EXAMPLE 51

3-Ethyl-4-(4-chloro-3-methylsulfamoyl-phenyl)-2-thiazolidone-4-ol is obtained according to Example 28 from 2-bromo-4'-chloro-3'-methyl-sulfamoyl-acetophenone and ethylammonium-N-ethylthiocarbamate. Amorphous solid material is obtained, decomposition starting at 120° C.

EXAMPLE 52

3-Ethyl-4-[4-chloro-3-(4-methylbenzylsulfamoyl)-phenyl]-2-thiazolidone-4-ol is obtained according to Example 28 from 2-bromo-4'-chloro-3'-(4-methyl-benzyl-sulfamoyl)-acetophenone and ethylammonium-N-ethylthiocarbamate. Decomposition starts at 125° C.

EXAMPLE 53

5-Ethyl-4-(4-chloro-3-sulfamoyl-phenyl)-3-methyl-2-thiazolidone-4-ol is obtained according to Example 28 by reacting 2-bromo-4'-chloro-3'-sulfamoyl-butyrophenone with methylammonium-N-methyl-thiocarbamate. Amorphous solid matter is obtained, decomposition point: 100° C.

EXAMPLE 54

4-(4-Chloro-3-sulfamoyl-phenyl)-3,5-dimethyl-2-thiazolidone-4-ol is obtained according to Example 25 from 2-bromo-4'-chloro-3'-sulfamoyl-propiophenone and methylammonium-N-methylthiocarbamate. Decomposition starts at 120° C.

EXAMPLE 55

4-[4-Chloro-3-(4-methylbenzyl-sulfamoyl)-phenyl]-3-methyl-2-thiazolidone-4-ol is obtained according to Example 25 from 2-bromo-4'-chloro-3'-(4-methyl-benzyl-sulfamoyl)-acetophenone and methylammonium-N-methylthiocarbamate. The melting point is 144° C., decomposition starting at 160° C.

EXAMPLE 56

3-Allyl-4-(4-chloro-3-sulfamoyl-phenyl)-2-thiazolidone-4-ol is obtained according to Example 25 from allylammonium-N-allyl-thiocarbamate and 2-bromo-4'-chloro-3'-sulfamoyl-acetophenone. Melting point: 177° C. (from acetonitrile).

EXAMPLE 57

3-Ethyl-4-(4-bromo-3-sulfamoyl-phenyl)-2-thiazolidone-4-ol is obtained according to Example 25 from 2,4'-dibromo-3'-sulfamoyl-acetophenone and ethylammonium-N-ethyl-thiocarbamate. Melting point: 165° C. (decomposition).

EXAMPLE 58

4-(4-Bromo-3-sulfamoyl-phenyl)-3-methyl-2-thiazolidone-4-ol is obtained according to Example 25 from 2,4'-dibromo-3'-sulfamoyl-acetophenone and methylammonium-N-methylthiocarbamate. Melting point: 172° C. (decomposition).

EXAMPLE 59

5-Ethyl-4-(4-chloro-3-sulfamoyl-phenyl)-3-methyl-2-thiazolidone-4-ol is obtained according to Example 25 from 2-bromo-4'-chloro-3'-sulfamoyl-butyrophenone and methylammonium-N-methylthiocarbamate. Decomposition starts at 130° C.

EXAMPLE 60

3-Ethyl-4-(4-chloro-3-methylsulfamoyl-phenyl)-5-methyl-2-thiazolidone-4-ol is obtained according to Example 25 from 2-bromo-4'-chloro-3'-methylsulfamoyl-propiophenone and ethylammonium-N-ethylthiocarbamate. Melting point: 165° C. (decomposition).

EXAMPLE 61

4-(3-Benzylsulfamoyl-4-chloro-phenyl)-3,5-dimethyl-2-thiazolidone-4-ol is obtained according to Example 25 from 3'-benzylsulfamoyl-2-bromo-4'-chloro-propiophenone and methylammonium-N-methylthiocarbamate. Melting point: 140° C. (decomposition).

EXAMPLE 62

4-(4-Chloro-3-isobutylsulfamoyl-phenyl)-3-methyl-2-thiazolidone-4-ol is obtained according to Example 25 from 2-bromo-4'-chloro-3'-isobutyl-acetophenone and methylammonium-N-methylthiocarbamate. Melting point: 179° C. (decomposition).

EXAMPLE 63

3-Allyl-4-(4-bromo-3-sulfamoyl-phenyl)-2-thiazolidone-4-ol is obtained according to Example 32 by reacting allylammonium-N-allylthiocarbamate and 2,4'-dibromo-3'-sulfamoylacetophenone. Melting point: 138° C. (decomposition).

EXAMPLE 64

4-(4-Chloro-3-sulfamoyl-phenyl)-3-isobutyl-2-thiazolidone-4-ol is obtained according to Example 32 from 2-bromo-4'-chloro-3'-sulfamoyl-acetophenone and isobutylammonium-N-isobutylthiocarbamate. Melting point: 140° C. (decomposition) from ethyl acetate/diisopropylether.

EXAMPLE 65

4-(4-Chloro-3-sulfamoyl-phenyl)-3-isobutyl-5-methyl-2-thiazolidone-4-ol is obtained according to Example 32 from 2-bromo-4'-chloro-3'-sulfamoyl-propiophenone and isobutylammonium-N-isobutyl-thiocarbamate. Decomposition point: 117° to 121° C.

EXAMPLE 66

5-Ethyl-4-(4-chloro-3-sulfamoyl-phenyl)-3-isobutyl-2-thiazolidone-4-ol is obtained according to Example 32 from 2-bromo-4'-chloro-3'-sulfamoyl-butyrophenone and isobutylammonium-N-isobutylthiocarbamate. Decomposition point: 101° C.

EXAMPLE 67

4-(3,4-Dichloro-5-sulfamoyl-phenyl)-3-methyl-2-thiazolidone-4-ol 1.22 Grams (0.01 mole) of methylammonium-N-methyl-thiocarbamate are introduced under a nitrogen atmosphere into 20 ml of ethanol, and 3.03 g of 2,3',4'-trichloro-5'-sulfamoylacetophenone are added portionwise, while stirring. The reaction mixture is stirred over night at room temperature, then it is slowly introduced into 60 ml of water, while triturating and stirring vigorously, and the crystals are filtered off. Melting point: 188° C. (decomposition).

EXAMPLE 68

4-(2,4-Dichloro-5-sulfamoyl-phenyl)-3-methyl-2-thiazolidone-4-ol is obtained according to Example 67 from 2-bromo-2',4'-dichloro-5'-sulfamoyl-acetophenone and methylammonium-N-methyl-thiocarbamate. Melting point: 203° C. (decomposition).

EXAMPLE 69

4-(4-Chloro-3-sulfamoyl-phenyl)-3-methyl-2-thiazolidone-4-ol

A solution of 1.15 g (0.02 mole) of methylisocyanate in 5 ml of anhydrous tetrahydrofuran is added dropwise under a nitrogen atmosphere and with the exclusion of air humidity to a solution of 5.32 g (0.02 mole) of 4'-chloro-2-mercapto-3'-sulfamoyl-acetophenone in 60 ml of anhydrous tetrahydrofuran which is stirred and cooled to 0° C.–5° C. The mixture is then stirred for 20 hours at room temperature and subsequently for another 2 hours at a temperature of from 33° to 35° C. After eliminating the solvent by distillation in vacuo at a bath temperature of less than 35° C., the residue is dissolved in a mixture of acetone and ethyl acetate, and the substance is separated by column chromatography with silica gel. Melting point: 179° to 181° C. (decomposition).

EXAMPLE 70

4-(4-Chloro-3-sulfamoyl-phenyl)-3-methyl-2-thiazolidine-thione-4-ol is obtained according to Example 69 by reacting 4'-chloro-2-mercapto-3'-sulfamoyl-acetophenone with methyl-isothiocyanate. Melting point: 216° to 218° C. (decomposition).

The thio- and dithio-carbamates used in the above Examples as starting compounds have been prepared according to methods known in the literature [cf. Houben-Weyl, "Methoden der Org. Chemie", IVth edition, Vol. IX (1955) page 823; Arch. Pharm. 293, 957 (1960)].

The uncorrected decomposition points, which strongly depend on the heating rate, of the individual compounds of the formula III

have been specified in the following Table:

| $R^1$ | Z | M | Decomposition point |
|---|---|---|---|
| $CH_3$ | S | $CH_3\overset{\oplus}{N}H_3$ | 115 – 117° |
| $C_2H_5$ | S | $C_2H_5\overset{\oplus}{N}H_3$ | 99 – 102° |
| $CH_3CH_2CH_2$ | S | $(C_2H_5)_3\overset{\oplus}{N}H$ | 95 – 97° |
| $(CH_3)_2CH$ | S | $(C_2H_5)_3\overset{\oplus}{N}H$ | 108 – 111° |
| $CH_2=CH-CH_2$ | S | $(C_2H_5)_3\overset{\oplus}{N}H$ | 100 – 103° |
| $CH_3CH_2-\underset{CH_3}{\overset{|}{CH}}$ | S | $CH_3CH_2\underset{CH_3}{\overset{|}{CH}}-\overset{\oplus}{N}H_3$ | 112 – 113° |
| $(CH_3)_2CH-CH_2$ | S | $(CH_3)_2CH-CH_2-\overset{\oplus}{N}H_3$ | 126° |
| 2-pyridyl-$CH_2$ | S | $(C_2H_5)_3\overset{\oplus}{N}H$ | 77° |
| 3-pyridyl-$CH_2$ | S | $(C_2H_5)_3\overset{\oplus}{N}H$ | 98 – 100° |
| 4-pyridyl-$CH_2$ | S | $(C_2H_5)_3\overset{\oplus}{N}H$ | 123 – 125° |
| $CH_3$ | O | $CH_3\overset{\oplus}{N}H_3$ | 97 – 100° |
| $C_2H_5$ | O | $C_2H_5\overset{\oplus}{N}H_3$ | 112 – 114° |
| $CH_3CH_2CH_2$ | O | $CH_3CH_2CH_2\overset{\oplus}{N}H_3$ | 116 – 119° |
| $(CH_3)_2CH$ | O | $(CH_3)_2CH\overset{\oplus}{N}H_3$ | 108 – 111° |
| $CH_2=CH-CH_2$ | O | $CH_2=CH-CH_2\overset{\oplus}{N}H_3$ | 92 – 94° |
| $CH_3-CH_2-\underset{CH_3}{\overset{|}{CH}}$ | O | $CH_3CH_2-\underset{CH_3}{\overset{|}{CH}}-\overset{\oplus}{N}H_3$ | 105 – 108° |
| $(CH_3)_2CH-CH_2$ | O | $(CH_3)_2CH-CH_2\overset{\oplus}{N}H_3$ | 113 – 115° 94 – 96° |
| 2-pyridyl-$CH_2$ | O | 2-pyridyl-$CH_2\overset{\oplus}{N}H_3$ | |
| 3-pyridyl-$CH_2$ | O | 3-piperidyl-$CH_2\overset{\oplus}{N}H_3$ | 86 – 88° |
| $CH_3(CH_2)_3$ | S | $Na^\oplus$ | 64° (from ethyl acetate) |

We claim:

1. A compound selected from the group consisting of thiazolidine derivatives of the formula

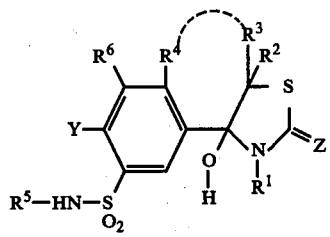

wherein $R^1$ is alkyl of from 1 to 4 carbon atoms, alkenyl of from 1 to 4 carbon atoms or pyridylmethyl; each of $R^2$ and $R^3$ is hydrogen or alkyl of from 1 to 3 carbon atoms, each of $R^4$ and $R^6$ is hydrogen or halogen, one of $R^4$ and $R^6$ being hydrogen, or $R^3$ and $R^4$ together may be alkylidene of up to 5 carbon atoms, ethylene, propylene or methylethylene; $R^5$ is hydrogen, alkyl of from 1 to 4 carbon atoms, benzyl, or benzyl substituted in the aromatic nucleus by chlorine or methyl; Y is halogen; and Z is oxygen or sulfur;

and pharmaceutically acceptable acid addition salts thereof.

2. The thiazolidine derivative as defined in claim 1, which is 4-(4-chloro-3-sulfamoyl-phenyl)-3-methyl-2-thiazolidone-4-ol.

3. The thiazolidine derivative as defined in claim 1, which is 4-(4-chloro-3-sulfamoyl-phenyl)-3,5-dimethyl-2-thiazolidone-4-ol.

4. The thiazolidine derivative as defined in claim 1, which is 4-(4-bromo-3-sulfamoyl-phenyl)-3-methyl-2-thiazolidone-4-ol.

5. The thiazotidine derivative as defined in claim 1, which is 5-ethyl-4-(4-chloro-3-sulfamoyl-phenyl)-3-methyl-2-thiazolidone-4-ol.

6. The thiazolidine derivative as defined in claim 1, which is 6-chloro-3a-hydroxy-3-methyl-5-sulfamoyl-8H-indeno-[2,1-b]-thiazolidine-2-thione.

7. The thiazolidine derivative as defined in claim 1, which is 6-chloro-3a-hydroxy-3-methyl-5-sulfamoyl-8H-indeno-[2,1-b]-thiazolidine-2-one.

8. The thiazolidine derivative as defined in claim 1, which is 6-chloro-3a-hydroxy-3,9-dimethyl-5-sulfamoyl-8H-indeno-[2,1-b]-thiazolidine-2-one.

9. The thiazolidine derivative as defined in claim 1, which is 3-ethyl-6-chloro-3a-hydroxy-5-sulfamoyl-8H-indeno-[2,1-b]-thiazolidine-2-one.

10. The thiazolidine derivative as defined in claim 1, which is 3-ethyl-6-chloro-3a-hydroxy-5-sulfamoyl-8H-indeno-[2,1-b]-thiazolidine-2-thione.

11. A method of effecting salidiuresis which comprises administering to a patient in need of salidiuretic treatment an amount of a compound as defined in claim 1 sufficient to effect salidiuresis.

12. A salidiuretic composition, in the form of a tablet, dragée, capsule, suppository or ampule, which comprises a compound as defined in claim 1, in an amount sufficient to effect salidiuresis, and a pharmaceutically usual filler or carrier substance.

13. A composition as defined in claim 12 wherein said thiazolidine derivative is present in an amount of from 5 to 500 mg. per tablet.

14. A composition as defined in claim 13, wherein said thiazolidine derivative is present in an amount of 10 to 100 mg. per tablet.